US00PP32364P2

(12) United States Plant Patent
Meyer

(10) Patent No.: US PP32,364 P2
(45) Date of Patent: Oct. 20, 2020

(54) ***HEMEROCALLIS* PLANT NAMED 'INKHEART'**

(50) Latin Name: ***Hemerocallis* (L.) hybrid**
Varietal Denomination: Inkheart

(71) Applicant: Chris Meyer, Zeeland, MI (US)

(72) Inventor: Chris Meyer, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,089

(22) Filed: Jan. 30, 2020

(51) Int. Cl.
*A01H 5/02* (2018.01)
*A01H 6/00* (2018.01)

(52) U.S. Cl.
USPC ..... Plt./312
CPC ..... *A01H 6/00* (2018.05)

(58) Field of Classification Search
USPC ..... Plt./312
CPC ..... A01H 6/00
See application file for complete search history.

*Primary Examiner* — Anne Marie Grunberg

(57) ABSTRACT

A new and distinct *Hemerocallis* plant named 'Inkheart' characterized by winter-hardy compact habit with clean medium-green foliage that goes dormant in the winter. The flowers are rounded, fragrant, single, creamy-yellow, with a wide dark-purple eye band and matching picotee edge and greenish-yellow throat. Tepals are slightly reflexed near apices with the outer tepal set having consistent, considerable, dark-purple crisped margins. The new plant flowers on stems up to 58 cm tall with four-way branching beginning about mid-July and repeating late into summer.

1 Drawing Sheet

Botanical classification: *Hemerocallis* (L.) hybrid.
Variety denomination: 'Inkheart'.

STATEMENT REGARDING PRIOR DISCLOSURES UNDER 37 CFR 1.77(b)(6)

The first non-enabling disclosure was the brief description and photograph on a website maintained by Walters Gardens, Inc. on Feb. 1, 2019. Subsequently, on May 29, 2019 the new plant was advertised in the "Walters Gardens 19-20 Catalog" followed by a number of sales made by Walters Gardens, Inc. on Jul. 8, 2019. Walters Gardens, Inc. obtained the new plant and all information relating to the new plant, from the inventor. No plants of *Hemerocallis* 'Inkheart' have been sold in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct daylily plant, *Hemerocallis* 'Inkheart' hereinafter also referred to as the new plant or just the cultivar name, 'Inkheart'. *Hemerocallis* 'Inkheart' was hybridized by the inventor, Chris Meyer, in the spring of 2005 in a greenhouse at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was 'Bridgeton Gem' (not patented) and the male or pollen parent was 'Rock Solid' (not patented). The new plant was selected as a single seedling from this cross, and after confidential evaluations in a trial bed beginning in 2008 in Zeeland, Mich. was assigned the breeder code 05-681-4. The new plant has been asexually propagated by division at the same wholesale nursery in Zeeland, Mich. since 2009 with all resultant asexually propagated plants having retained all the same unique traits as the original plant. *Hemerocallis* 'Inkheart' is stable and reproduces true to type in successive generations of asexual reproduction.

There are nearly 90,000 registered daylilies with The American *Hemerocallis* Society, which is the International Cultivar Registration Authority for the genus *Hemerocallis*. In comparison to the new plant, the female parent has a cream flower color with a burgundy eye and picotee margin of the inner tepals, a yellow-green throat. In comparison to the new plant, the male parent has a creamy-cranberry flowers with broad plum violet eye and matching broad picotee margin with more reflexed petals on slightly taller scapes.

The most similar daylily known to the inventor are: 'Chasing Dragonflies' (not patented), 'Graphic Design' (not patented) and 'Kaleb David Erikson' (not patented).

'Chasing Dragonflies' a similar tepal color with thinner and lighter reddish-purple picotee margin and lighter, violet-blue, two-toned eyed and the foliage is semi-evergreen. 'Graphic Design' has flowers with lighter cream tepals, much broader picotee margin and the foliage is semi-evergreen. 'Kaleb David Erikson' tepals with a cream-ivory color and much thinner picotee margin and matching eye of lighter reddish-purple.

*Hemerocallis* 'Inkheart' differs from all other daylilies known to the applicant, by the combination of the following traits:

1. Winter-hardy, compact habit with clean medium-green foliage that goes dormant in the winter;

2. Fragrant, single, limbate, rounded flowers about 12.5 cm across of creamy-yellow with a very wide dark-purple eye zone and matching ruffled picotee edge and greenish-yellow throat;
3. Outer tepals with consistent, considerable, dark-purple crisped margins.
4. Tepals slightly reflexed near apices;
5. Plants produce four-way branched scapes of about 56 cm tall with up to 16 flowers per scape;
6. Flowering begins about mid to late-July with excellent coverage and repeat flowering late in the season;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
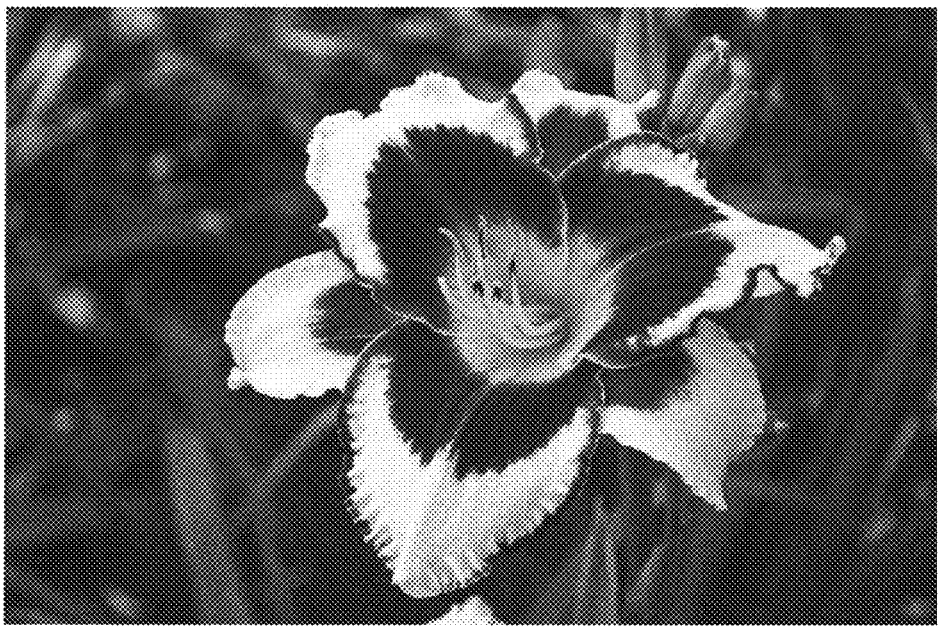
FIG. 1 shows a close-up of a flower and bud.
Figure 2:
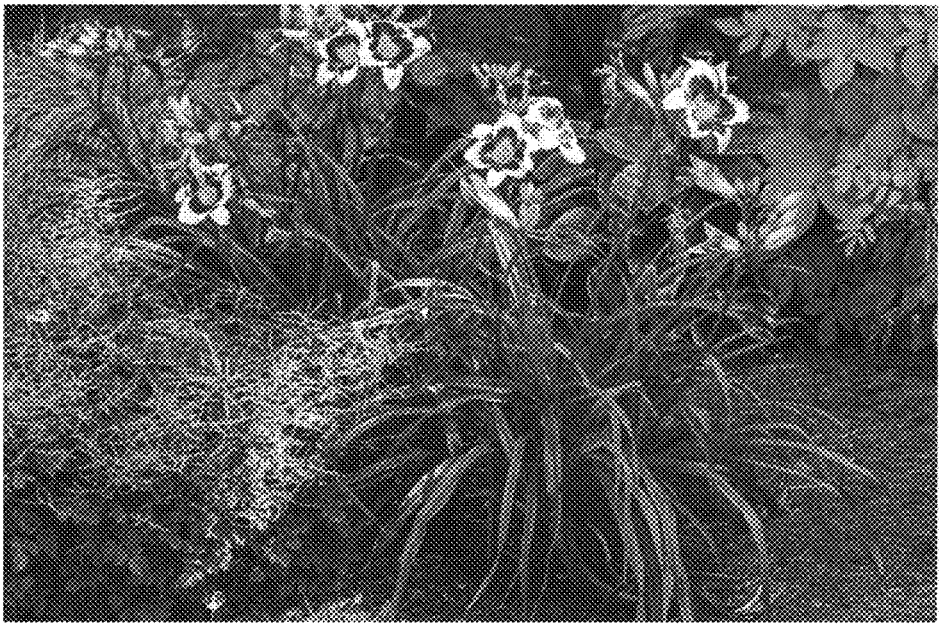
FIG. 2 shows a three-year-old plant in peak flower in a sunny landscape during mid-summer at a display garden in Zeeland, Mich.

The following descriptions and color references are based on the 2015 edition of The Royal Horticultural Society Colour Chart except where common dictionary terms are used. The new plant, *Hemerocallis* 'Inkheart', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Mich. with and supplemental water and fertilizer.

Botanical classification: *Hemerocallis* (L.) hybrid;

Parentage: Female (seed) parent is 'Bridgeton Gem'; male (pollen) is 'Rock Solid';

Propagation: Division of the rhizome;

Growth rate: Moderate to rapid;

Crop time: About 8 to 10 weeks to flower starting in spring in a 3.8 liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with four basal shoots emerging from rhizomes producing a radially symmetrical mound of arching leaves;

Plant size: Foliage height about 38.0 cm tall from soil line to the top of the leaves and about 88.0 cm wide at the widest point;

Leaves: Entire, glabrous, slightly glaucous abaxial and adaxial, linear, sessile; folded; apex narrowly acute, base sheathing; to about 67.5 cm long and 29.0 mm across, average about 61.0 cm long and about 24.0 mm across; about 20 leaves per division;

Cauline leaves: 1 to 2 per scape; reduced, average about 4.5 cm long and 8.0 mm across;

Leaf color: Young adaxial nearest RHS 137A; young abaxial nearest RHS 138B; mature adaxial nearest RHS 137A; mature abaxial nearest RHS 138A;

Veins: Parallel; color adaxial between RHS 137A and RHS NN137D, and abaxial nearest RHS 138A;

Flower description:

Flowers: Funnelform; single, with two sets of three tepals; zygomorphic, incomplete; up to 19 per scape, mostly distally arranged on typically 4 branches; upward and outwardly facing; about 12.5 cm across and 11.5 cm tall to exserted stigma, corolla about 7.0 cm deep; individually lasting for about one day; peduncle remains effective from mid-July into early-August for approximately three weeks in Zeeland, Mich. with repeating into October;

Flower fragrance: Lightly sweet;

Buds one day prior to opening: Oblate ellipsoid with bluntly acute apex and tepals beginning to separate, and basal one-fifth narrowed terete; about 92.0 mm long and about 28.0 mm in diameter at widest point with basal one-fifth narrowing to about 11.0 mm diameter;

Bud color one day from opening: Apical 5.0 mm nearest RHS 24B with undertone of nearest RHS 146D, central portion nearest RHS 24B, developing an undertone of nearest RHS 146D toward base, basal 5 mm between RHS 146C and RHS 146D;

Tepals: 2 sets of 3;

Inner tepals: Rounded; glabrous; rounded apex; consistently and moderately crisped margins to about 3.0 mm deep; base truncate, fused in proximal 20.0 mm; width at fusion about 10.0 mm; midrib fluted abaxial and costate adaxial about 2.0 mm wide; slightly recurved about 45 degrees in distal one-quarter; about 6.2 cm across at widest point and about 11.3 cm long;

Outer tepals: Broadly lanceolate to elliptic; glabrous; acute apex; base fused in proximal 20 mm; irregularly sinuate margin to about 5.0 mm wide, central portion flat; tepals reflexed about 90 degrees in distal one-fifth; about 11.0 cm long and 4.0 cm across;

Inner tepal color: Adaxial margin of 1.0 to 5.0 mm wide nearest RHS N79A, distal face nearest RHS 22D, 2.0 cm wide eye nearest RHS N79A diffusing proximally to RHS 10C, longitudinal center and base nearest RHS 150C; abaxial 2.0 mm wide margin nearest RN79A, distal center between RHS 24C and RHS 23D with undertone near center nearest RHS N79A, basal 3.0 cm between RHS 151D and RHS 150C;

Outer tepal color: Adaxial center between RHS 25C and RHS 25D, without margin, eye between RHS N79A and RHS N79B, distal base inside eye nearest RHS 16B transitioning proximally to a blend between RHS 145B and RHS 150B; abaxial apex between RHS 146D and RHS 144A, distal center between a blend of RHS 168D and RHS 23C with slight undertone of in middle of nearest RHS N79A, base between RHS 145B and RHS 150;

Pedicel: Cylindrical; to approximately 14.0 mm long, average 8.0 mm long and 6.0 mm diameter at base;

Pedicel color: Nearest blend between RHS 138A and RHS 146B;

Peduncle: Three to five per plant during peak initial flowering and two per plant with repeat flowering, erect to about 58.0 cm tall and 9.0 mm diameter at base, average 55.0 cm tall; extending above foliage;

Peduncle color: Nearest blend between RHS 138A and RHS 146B;

Gynoecium: Single; tri-carpelled; glabrous; about 10.6 cm long;

*Style.*—Single, about 9.8 cm long, 2.0 mm diameter, slightly arcuate upward at distal one-fifth; color distally nearest RHS 28D, base nearest RHS 1D.

*Stigma.*—1.0 mm to 2.0 mm in diameter; color nearest RHS 18C.

*Ovary.*—Ellipsoidal; smooth; acute apex, truncate base; about 7.0 mm long and 4.0 mm diameter at base; color nearest RHS 145A.

Androecium: Six; glabrous;

*Filaments.*—Six; cylindrical; adnate to inner tepal in basal 18.0 mm above ovary; arcuate upward in distal 10 mm; free in distal 62.0 mm long from fusion point on tepal; 80.0 mm long; basally applanate; 3.5 mm across and 2.0 mm thick; color distally nearest RHS 16B distally, middle nearest RHS 16B with slight blush of nearest RHS 187A and base blend between RHS 151D and RHS NN155D.

*Anthers.*—Oblong; dorsifixed, longitudinal; about 9.0 mm long and 2.0 mm wide; color closest to RHS N77A.

*Pollen.*—Elliptical, less than 0.1 mm long; color nearest RHS 17A.

Fruit and seeds have not been observed;

Disease and pest resistance and tolerance: 'Inkheart' has not shown resistance to diseases and pests beyond that common for daylilies, and given the northern testing regions the new plant has not been exposed to daylily rust, *Puccinia hemerocallidis*. The plant grows best and shows best coloration with plenty of moisture, adequate drainage and light shade during the hottest period of the day, but is able to tolerate some drought when mature and direct sun without leaf burn when provided sufficient water.

Hardiness at least from USDA zone 3 through 9, and other disease resistance and tolerance is typical of that of other daylilies. The new plant is useful for landscaping en masse, as a single specimen or small groups.

The invention claimed is:

1. A new and distinct ornamental daylily, *Hemerocallis* plant named 'Inkheart', as herein described and illustrated.

* * * * *